(12) United States Patent
Kälberer et al.

(10) Patent No.: US 6,224,633 B1
(45) Date of Patent: May 1, 2001

(54) HIP JOINT PROSTHESIS

(75) Inventors: Hartmut Kälberer, Deizisau; Hans-Georg Pfaff, Ostfildern, both of (DE)

(73) Assignee: Cerasiv GmbH Innovatives Keramik-Engineering, Plochingen (DE)

( * ) Notice: Subject to any disclaimer, the term of this patent is extended or adjusted under 35 U.S.C. 154(b) by 0 days.

(21) Appl. No.: 09/091,620
(22) PCT Filed: Dec. 6, 1996
(86) PCT No.: PCT/EP96/05455
§ 371 Date: Dec. 17, 1999
§ 102(e) Date: Dec. 17, 1999
(87) PCT Pub. No.: WO97/22311
PCT Pub. Date: Jun. 26, 1997

(30) Foreign Application Priority Data

Dec. 19, 1995 (DE) .............................. 195 47 514
Dec. 20, 1995 (DE) .............................. 195 47 814
Jun. 12, 1996 (DE) .............................. 196 22 583

(51) Int. Cl.$^7$ ...................................... A61F 2/32
(52) U.S. Cl. .......................... 623/22.24; 623/22.28
(58) Field of Search ...................... 623/22.21, 22.24, 623/22.28, 22.29

(56) References Cited

U.S. PATENT DOCUMENTS

| | | | |
|---|---|---|---|
| 3,818,512 | * | 6/1974 | Shersher .............. 623/22.19 |
| 5,092,897 | * | 3/1992 | Forte .................. 623/22.18 |
| 5,549,700 | * | 8/1996 | Graham et al. ......... 623/22.14 |
| 5,725,589 | * | 3/1998 | Pfaff et al. .......... 623/22.29 |

* cited by examiner

Primary Examiner—David J Isabella
(74) Attorney, Agent, or Firm—Fulbright & Jaworski LLP

(57) ABSTRACT

The invention relates to a hip joint prothesis having a metallic prothesis shell (1) with a cavity insert (2) having a spherical recess (3) and with an intermediate element (4) which is made of plastics and arranged between the prothesis shell (1) and the cavity insert (2).

In order to avoid osteolysis, it is suggested that the intermediate element (4) consist of an upper portion (5) and a lower portion (6), that it be possible for upper portion (5) and lower portion (6) to be connected to each other, and that the cavity insert (2) be retained between upper portion (5) and lower portion (6).

19 Claims, 3 Drawing Sheets

HIP JOINT PROSTHESIS

BACKGROUND AND SUMMARY OF THE INVENTION

The invention relates to a hip joint prosthesis having a metallic prosthesis shell with a cavity insert having a spherical recess and with an intermediate element which is made of plastics and arranged between the prosthesis shell and the cavity insert.

A hip Joint prothesis having three spherical calottes which lie one inside the other is known from the utility model FR 2 715 828.

The spherical outer calotte consists of a bio-compatible, rigid material such as INOX-steel or titanium, and is provided, on the outside, with radial depressions for securing in the articular cavity of the pelvic bone.

The spherical inner calotte consists of a hard, bio-compatible material, such as aluminium oxide ceramic, for example, or of a similar material, having a low coefficient of friction in relation to the material of which the head of the femur element, which is connected thereto, consists.

The spherical intermediate calotte consists of a semi-rigid material such as plastics, in particular polyethylene.

A problem with intermediate calottes or intermediate elements made of plastics is that, as a result of high abrasion, they can trigger osteolysis if there is no form-locking connection between the sliding shell and the plastics coating. On the other hand, a form-locking connection can be achieved by melting the plastics coating, as described in EP 0 554 214 A1. This can, however, lead to destruction of the molecular structure and consequently can trigger wear.

The underlying object of the invention is to improve a hip joint prosthesis according to the preamble of claim 1, in such a way that the danger of osteolysis is eliminated to a considerable extent.

This object is achieved in accordance with the invention by the characterising features of claim 1.

As a result of the intermediate element consisting of an upper portion and a lower portion, it being possible for upper portion and lower portion to be connected to each other, and the cavity insert being retained between upper portion and lower portion, the wear of the intermediate element is avoided and consequently the danger of osteolysis is reduced.

In a preferred embodiment, the cavity insert is covered on all sides, with the exception of its spherical recess, by the intermediate element, i.e. by the upper portion and lower portion, so that there are no free places at which abrasion can occur.

The connection of the upper portion to the lower portion can be carried out in a whole variety of ways. Screw connections by way of a screw thread, snap connections, pinning, gluing or welding have proven advantageous.

The cavity insert can be produced from metal or ceramics. This invention is favorable suitable for all ceramic cavity inserts.

In an advantageous manner, there are provided in the cavity insert and in the adjacent lower portion, opposing openings in which are placed inserts for protecting against rotation. As a result of this, the cavity insert sits in the intermediate element in a manner such that it is fixed in its position. The inserts can be, for example, pins, slotting blocks and feather-key systems respectively, or wedges and can be made, for example, from metal or plastics. For improved fixing, the inserts advantageously fill the openings completely.

Further features of the invention result from the Figures, which are described in the following.

DETAILED DESCRIPTION OF PREFERRED EMBODIMENTS

Figure 1:
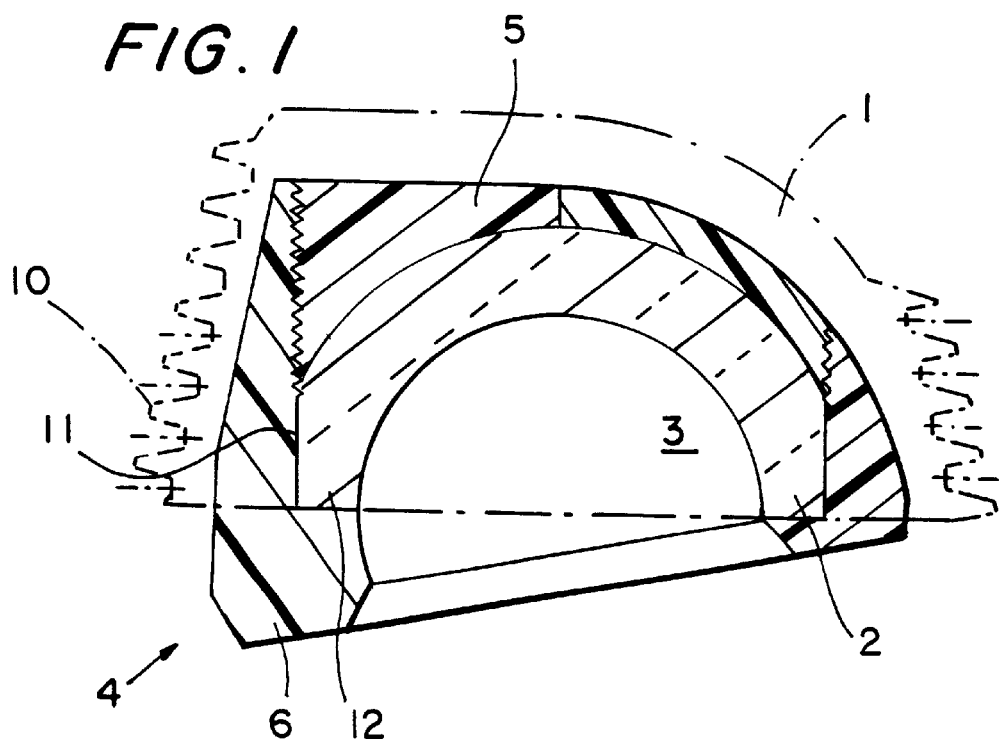
FIG. 1 is a preferred embodiment of the prosthesis of the present invention that is particualry useful in a patient with a dysplasia.

FIG. 1 shows, in section, a metallic prosthesis shell 1, which can be implanted in the articular cavity (not shown) of a pelvic bone. For improved retention, ribs or a screw thread 10 are arranged on the outside of the prosthesis shell 1. Inserted into the prothesis shell 1 is an intermediate element 4 made of plastics, which intermediate element in turn covers a ceramic cavity insert 2.

The outer contour of the intermediate element 4 is matched to the shape of the prothesis shell 1, and the intermediate element consists of an upper portion 5 and a lower portion 6.

The lower portion 6 faces the femur bone and has a recess 11 for mounting of the cavity insert 2. In this connection, the cavity insert 2 is covered completely by the intermediate element 4, with the exception of its spherical recess 3. It should be emphasised in particular that the upper portion 5 also covers the supporting surface 12 which is adjacent to the recess 3. The upper portion 5 covers the cavity insert 2 on the rear side thereof and is connected to the lower portion 6 in a whole variety of ways. The spherical recess 3 is used to receive the head of a femur element.

Figure 2:
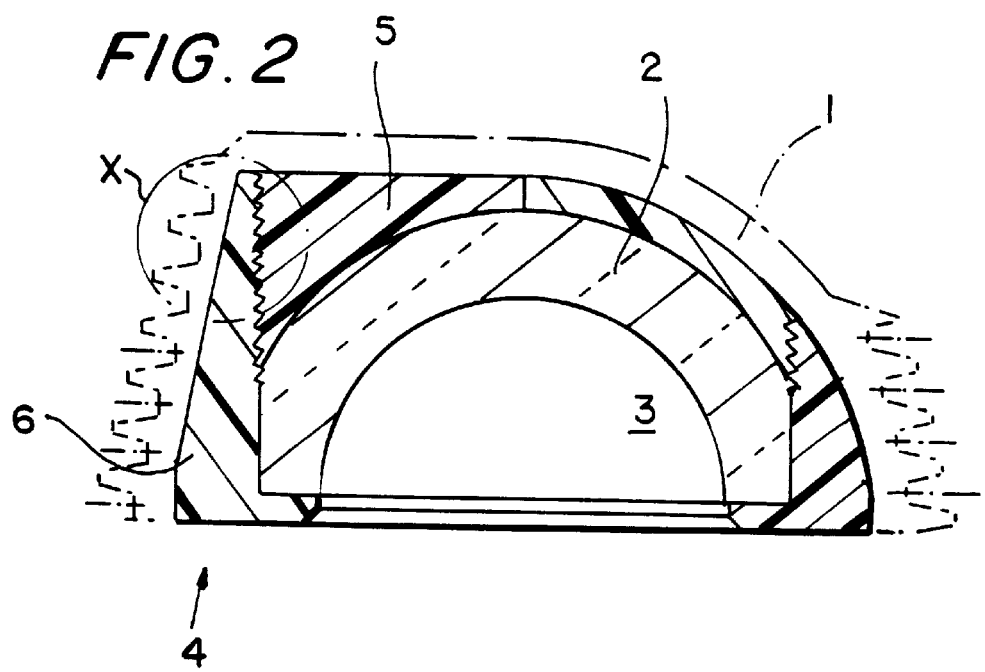
FIG. 2 is a symmetrical insertion of the cavity insert into the prosthesis shell.

FIG. 1 shows a design for the case that the patient has a dysplasia, i.e. if the cavity insert 2 has to be placed asymmetrically in the prothesis shell 1. FIG. 2 shows a symmetrical insertion of the cavity insert 2 into the prosthesis shell 1.

Figure 3:
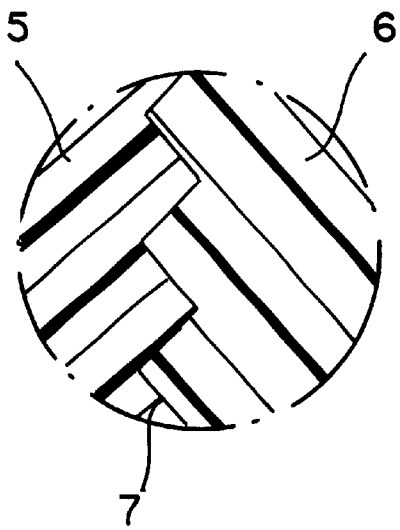
FIGS. 3 to 5 show various connections of the upper portion of the intermediate element to the lower portion of the intermediate element.
Figure 4:
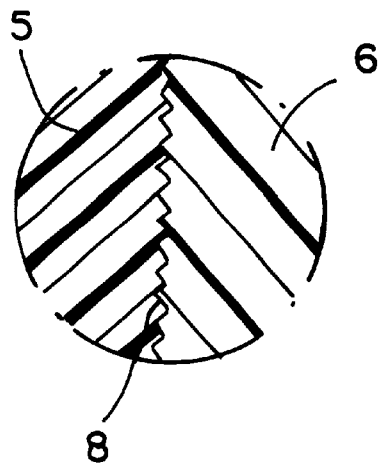
Figure 5:
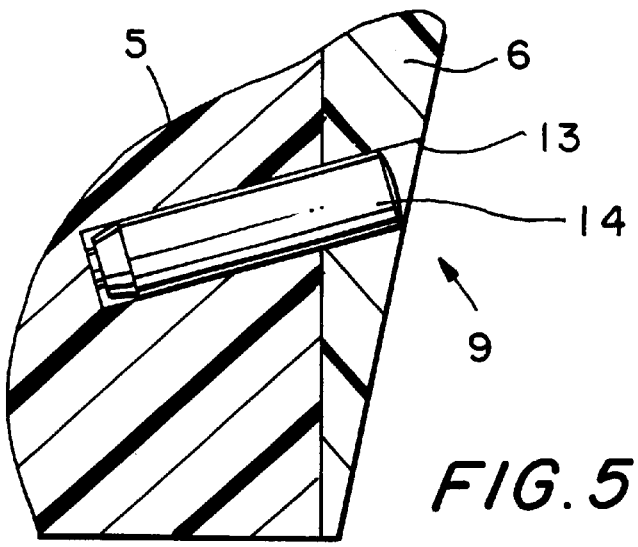
Figure 8:
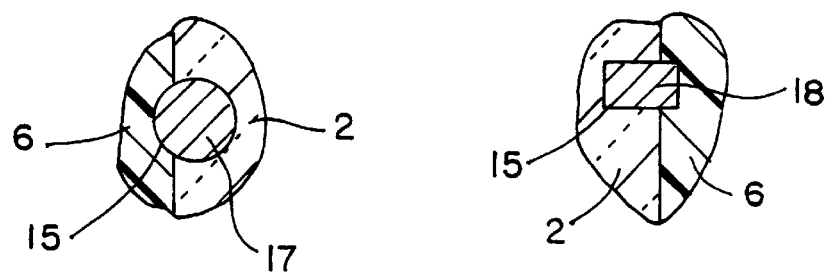
FIG. 8 shows a section along A—A of FIG. 7.

FIGS. 3 to 5 show various connections of the upper portion 5 to the lower portion 6. This connection is denoted with X in FIGS. 1 and 2. In FIG. 3, the upper portion 5 is connected or screwed to the lower portion 6 by way of a screw thread 7. FIG. 8 (sic) shows a snap connection 8. For this purpose, there are arranged on the upper portion 5 and lower portion 6 small individual projections, which engage in each other when the upper portion 5 is fitted into the lower portion 6 and thus create a good connection. FIG. 5 shows pinning 9. For this purpose, a bore 13 is introduced into the lower portion 6 and upper portion 5, in which bore a continuous pin 14 is inserted.

The cavity insert 2 consists of a ceramic material, such as an aluminium oxide ceramic, for example. All other ceramic materials can also be used, however.

Figure 6:
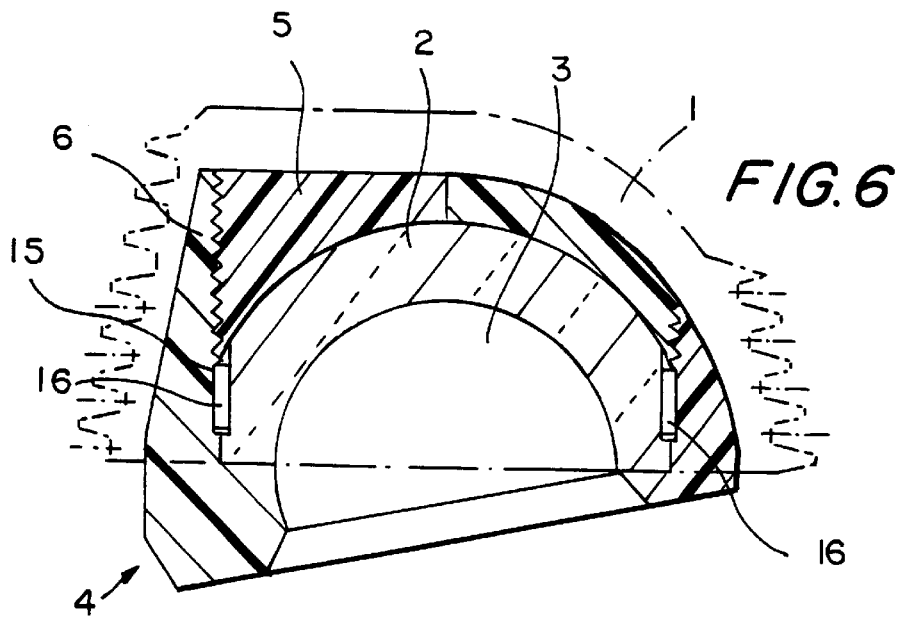
FIGS. 6 and 7 show preferred embodiments of prostheses according to the present invention.
Figure 7:
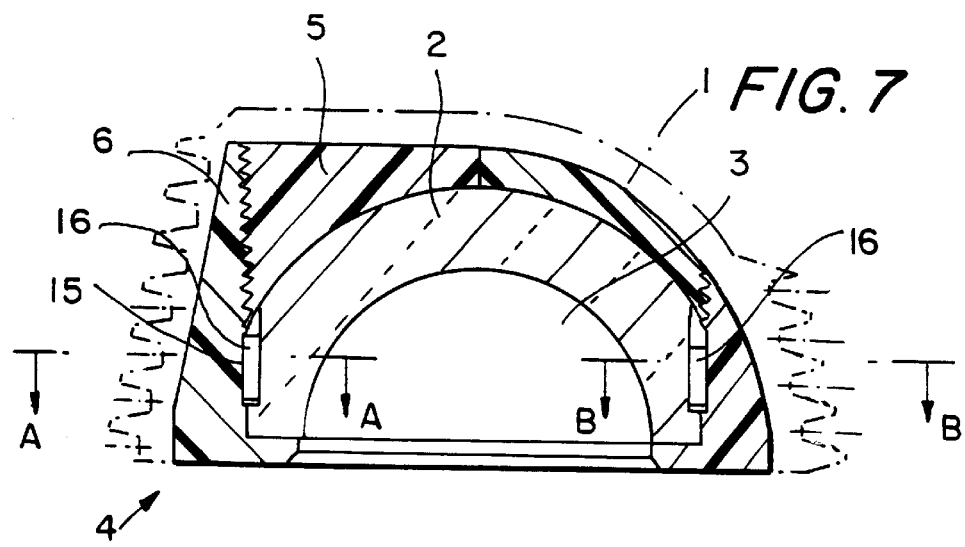

FIGS. 6 and 7 show embodiments similar to those shown in FIGS. 1 and 2; however, there are additionally provided in the cavity insert 2 and in the adjacent lower portion 6 opposing openings 15 in which are placed inserts 16 for protecting against rotation. These inserts 16 fill the openings 15 completely and consist of metal or plastics.

Figure 9:
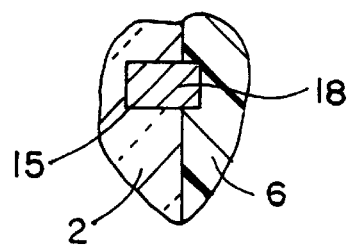
FIG. 9 shows a section aloing line B—B of FIG. 7.

FIG. 8 shows a section along the line A—A in FIG. 7 and FIG. 9 shows a section along the line B—B in FIG. 7. In FIG. 8, a pin 17, and in FIG. 9 a slotting block 18 which is rectangular in cross-section, is placed in the opening 15.

With these inserts 16, protection against torsion of the cavity insert 2 in the intermediate element 4 is achieved.

What is claimed is:

1. A hip joint prosthesis comprising
a cup shaped metal shell defining a cavity, a cavity insert configured to be disposed in said cavity, said insert having a spherical recess for engagement with an articulating joint element and a plastic intermediate element configured to be arranged between said shell and said cavity insert, wherein the intermediate element consists of separate upper portion and lower portion, said upper portion and lower portion are configured to be attached and connected to each other, and in that the cavity insert is retained between the connected upper and lower portions.

2. A hip joint prosthesis according to claim 1, wherein said upper portion is connected to the lower portion by a connector selected from the group consisting of a screw thread, a snap connection, a pin, a glue, and a weld.

3. A hip joint prosthesis according to one of the claim 1, wherein said cavity insert comprises at least one ceramic material.

4. A hip joint prosthesis according to claim 3, wherein said inserts are selected from the group consisting of a pin, a slotting block and a wedge.

5. A hip joint prosthesis according to claim 3, characterized in that said inserts fill said openings completely.

6. A hip joint prosthesis according to claim 3, wherein said inserts are made of a material selected from the group consisting of a metal and a plastic.

7. A hip joint prosthesis according to claim 4, wherein said inserts are made of a material selected from the group consisting of a metal and a plastic.

8. A hip joint prosthesis according to claim 5, wherein said inserts are made of a material selected from the group consisting of a metal and a plastic.

9. A hip joint prosthesis according to claim 1, wherein the upper portion is connected to the lower portion by a connector selected from the group consisting of a screw thread, a snap connection, a pin, a glue and a weld.

10. A hip joint prosthesis according to one of the claim 1, wherein said cavity insert comprises ceramic material.

11. A hip joint prosthesis according to one of the claim 2, wherein said cavity insert comprises ceramic material.

12. A hip joint prosthesis according to claim 4, wherein said inserts fill said openings completely.

13. A hip joint prosthesis according to claim 4, wherein said inserts are made of a material selected from the group consisting of a metal and a plastic.

14. A hip joint prosthesis according to claim 5, wherein said inserts are made of a material selected from the group consisting of a metal and a plastic.

15. A hip joint prosthesis according to claim 1, wherein the intermediate element surrounds said cavity insert except for said spherical recess.

16. A hip joint prosthesis according to claim 1, further comprising inserts which are shaped to be placed into opposing openings formed in said cavity insert and said lower portions for preventing rotation therebetween.

17. A hip joint prosthesis according to claim 1, further comprising inserts which are shaped to be placed into opposing openings formed in said cavity insert and said lower portions for preventing rotation therebetween.

18. A hip joint prosthesis according to claim 2, further comprising inserts which are shaped to be placed into opposing openings formed in said cavity insert and said lower portions for preventing rotation therebetween.

19. A hip joint prosthesis according to claim 3, further comprising inserts which are shaped to be placed into opposing openings formed in said cavity insert and said lower portions for preventing rotation therebetween.

* * * * *

UNITED STATES PATENT AND TRADEMARK OFFICE
CERTIFICATE OF CORRECTION

PATENT NO. : 6,224,633 B1
DATED : May 1, 2001
INVENTOR(S) : Kälberer et al.

It is certified that error appears in the above-identified patent and that said Letters Patent is hereby corrected as shown below:

Title page,
Under Foreign Application Priority Data, change "June 12, 1996" to -- Jun. 5, 1996 --.

Column 1,
Line 10, change "Joint" to -- joint --.

Signed and Sealed this

Twenty-seventh Day of November, 2001

Attest:

NICHOLAS P. GODICI
*Acting Director of the United States Patent and Trademark Office*

*Attesting Officer*